(12) United States Patent
Meseguer et al.

(10) Patent No.: US 7,396,947 B2
(45) Date of Patent: Jul. 8, 2008

(54) CHIRAL LIGANDS FOR APPLICATION IN ASYMMETRIC SYNTHESES

(75) Inventors: Benjamin Meseguer, Tarragona (ES); Dieter Arlt, Lemgo (DE)

(73) Assignee: LANXESS Deutschland GmbH, Leverkusen (DE)

( * ) Notice: Subject to any disclaimer, the term of this patent is extended or adjusted under 35 U.S.C. 154(b) by 0 days.

(21) Appl. No.: 10/571,722

(22) PCT Filed: Jun. 2, 2004

(86) PCT No.: PCT/EP2004/005930

§ 371 (c)(1),
(2), (4) Date: Mar. 13, 2006

(87) PCT Pub. No.: WO2004/111063

PCT Pub. Date: Dec. 23, 2004

(65) Prior Publication Data

US 2007/0004927 A1    Jan. 4, 2007

(30) Foreign Application Priority Data

Jun. 13, 2003  (DE) ............... 103 27 109
Aug. 12, 2003  (DE) ............... 103 37 013

(51) Int. Cl.
    *C07F 7/26*    (2006.01)
(52) U.S. Cl. .......................... 556/7; 558/72
(58) Field of Classification Search ............ 556/7; 558/72
    See application file for complete search history.

(56) References Cited

U.S. PATENT DOCUMENTS

| | | | |
|---|---|---|---|
| 5,488,172 A | | 1/1996 | Cereghetti et al. |
| 5,801,261 A | * | 9/1998 | Laue et al. .................. 556/16 |
| 6,162,929 A | | 12/2000 | Foricher et al. |
| 6,288,280 B1 | * | 9/2001 | Kienzle et al. .................. 568/14 |
| 6,313,317 B1 | | 11/2001 | Sayo et al. |
| 6,340,107 B1 | | 1/2002 | Cappa et al. |
| 6,480,513 B1 | * | 11/2002 | Kapany et al. .................. 372/20 |
| 6,521,769 B1 | * | 2/2003 | Zhang .................. 556/19 |
| 6,545,153 B1 | * | 4/2003 | Butler et al. .................. 544/141 |
| 6,583,312 B2 | * | 6/2003 | Sirges et al. .................. 560/179 |
| 6,844,462 B2 | | 1/2005 | Drieben-Hölscher et al. |
| 2002/0128501 A1 | | 9/2002 | Zhang |

FOREIGN PATENT DOCUMENTS

JP      3146187    *    1/2000

OTHER PUBLICATIONS

Schmid, Rudolf, et al., "Axially Dissymmetric Bis(triaryl)phosphines in the Biphenyl Series, . . . ", *Helvetica Chimica Acta*, vol. 71. (1988), pp. 897-929.
Noyori, Ryoji, et al., "BINAP: An Efficient Chrial Element for Asymmetric Catalysis", *Acc. Chem. Res.* 1990, 23, pp. 345-350.
Zhang, Xiaoyong, et al., "Highly Enantioselective Hydrogenation of $\alpha,\beta$-Unsaturated Carboxylic Acids Catalyzed by $H_8$-BINAP-Ru(II) Complexes", *Synlett*, Jul. 1994, pp. 501-503.
Zhang, Zhaoguo, et al., "Synthesis of Chiral Bisphosphines with Tunable Bite Angles and Their Applications in Asymmetric Hydrogenation of $\beta$-Ketoesters", *Journal of Organic Chemistry*, 2000, 65, pp. 6233-6226.
Miyashita, Akira, et al., "Synthesis of Atropisomeric 2,2'-Bis(dicyclohexylphosphino)-6,6'-dimethyl-1, 1'-biphenyl (BICHEP) and Its Use in Rh(I)-catalyzed Asymmetric Hydrogenation of Prochiral Olefins", *Chemistry Letters*, 1989, p. 1851.
Mashima, Kazushi, et al., "Chemoselective asymmetric hydrogenation of $\alpha,\beta$-unsaturated carbonyl compounds to allylic alcohols catalysed by [Ir(binap)(cod)]$BF_4$-aminophosphine", *Journal of Organometallic Chemistry*, 428 (1992) p. 213.
Ikariya, Takao, et al., "Synthesis of Novel Chiral Ruthenium Complexes of 2,2'-Bys(diphenylphosphino)-1,1'-binaphthyl and their Use as Asymmetric Catalysts", *J. Chem. Soc., Chem. Commun.*, 1985, p. 922.
Noyorit, Ryoji, et al., "Rapid, productive and stereoselective hydrogenation of ketones", *Pure Appl. Chem.*, vol. 71, No. 8, (1999) pp. 1493-1501.

* cited by examiner

*Primary Examiner*—Yvonne Eyler
*Assistant Examiner*—Chukwuma O Nwaonicha
(74) *Attorney, Agent, or Firm*—Michael A. Miller

(57) ABSTRACT

The present invention relates to biarylbisphosphines and intermediates thereof. The scope of the invention further encompasses catalysts preparable from the biarylbisphosphines and their use in asymmetric syntheses.

13 Claims, No Drawings

CHIRAL LIGANDS FOR APPLICATION IN ASYMMETRIC SYNTHESES

The present invention relates to biarylbisphosphines and intermediates thereof. The scope of the invention further encompasses catalysts preparable from the biarylbisphosphines and their use in asymmetric syntheses.

Enantiomerically enriched biarylbisphosphines, especially those which derive from substituted binaphthyls and biphenyls, lead, as ligands of transition metal complex catalysts, often to good to very good enantioselectivity (see, for example, Helv. Chim. Acta 1988, 71, 897-929; Acc. Chem. Res. 1990, 23, 345-350; Synlett 1994, 501-503; Angew. Chem. 2001, 113, 40-75).

Steric and electronic factors, which are determined by the type and arrangement of substituents on the biaryl system and within the phosphine groups, influence both the enantioselectivity and the activity of the catalysts prepared from such ligands.

In individual cases, Rh and Ru catalysts of this type are used industrially for enantioselective C=C double bond isomerizations and for enantioselective hydrogenations. The number of such industrial processes has to date been restricted because the number of available ligands which can be used with success widely for a relatively large number of substrates is small. Instead, the extensive investigations in this field show that, owing to the fundamental substrate specificity of the catalyst which has often been "tailored" for a quite specific substrate, even slight changes within the same substrate group prevent the required enantiomeric purity from being achieved for a very similar product.

J. Org. Chem. 2000, 65, 6223-6226, WO 01/21625 disclose representatives of a novel group of biphenylbisphosphines bridged in the 6,6'-position, which, by variation of the length of the alkylene moiety within the bridging element, enable adjustment of the catalysts which are prepared from these ligands to certain substrates (here: β-keto esters), so that optimized enantioselectivities are achieved. As a result of the investigation published in J. Org. Chem., an optimized enantioselectivity is described for a catalyst having a ligand with a —(CH$_2$)$_4$— moiety as a bridging unit ("C4TunaPhos").

Independently of the aforementioned publications, a single representative of this ligand group was disclosed in EP-A 1 095 946.

However, there is still a need to provide a group of ligands and catalysts preparable therefrom, which enable both a generally high level of enantioselectivity and activity and permit adjustment to a certain substrate by variation of the substituents on the ligand system in a simple manner.

The present invention thus provides compounds of the formula (I)

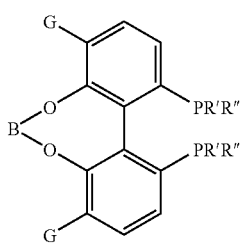

(1)

in which

B is a bivalent moiety of the formula —(CHR$^1$)$_n$—(R$^2$C=CR$^3$)—(CHR$^4$)$_m$ where R$^1$, R$^2$, R$^3$ and R$^4$ are each independently hydrogen or alkyl, preferably C$_1$-C$_6$-alkyl, and n and m are each independently zero or an integer from 1 to 8, where, however, the sum of n and m is from 1 to 8, preferably 2 or 4 and more preferably 2, and in which, moreover, G is chlorine or hydrogen, preferably hydrogen, and R' and R" are each independently aryl or alkyl or in which B is a bivalent moiety of the formula —(CHR$^1$)$_n$—(CR$^2$R$^3$)$_m$—(CHR$^4$)$_o$ where R$^1$, R$^2$, R$^3$ and R$^4$ are each independently hydrogen or alkyl, preferably C$_1$-C$_6$-alkyl, and n, m and o are each independently zero or an integer from 1 to 8, where, however, the sum of n, m and o is from 1 to 8, preferably 3 or 4, and in which, moreover, G is chlorine and R' and R" are each independently aryl or alkyl.

The invention encompasses both the pure stereoisomers and any mixtures thereof, especially racemic mixtures. Preference is given to the stereoisomerically enriched compounds of the formula (I) which have a stereoisomeric purity of 95% and more, more preferably 99% or more. In the case of compounds of the formula (I) that can occur in two enantiomeric forms, preference is accordingly given to an ee of 90% or more, particular preference to an ee of 98% and very particular preference to an ee of 99% or more.

In the context of the invention, all radical definitions, parameters and illustrations above and recited below, in general or within areas of preference, may be combined in any manner with one another, i.e. also between the particular areas and areas of preference.

In the context of the invention, enantiomerically enriched means enantiomerically pure compounds or mixtures of enantiomers of one compound in which one enantiomer is present in an enantiomeric excess, also referred to below as ee, in comparison to the other enantiomer. This enantiomeric excess is preferably from 10 to 100% ee, more preferably from 80 to 100% ee and most preferably from 95 to 100% ee.

The terms stereoisomer and stereoisomerically enriched are used in analogy for compounds for which diastereomers can also occur.

Alkyl represents, for example, unbranched, branched, cyclic or acyclic C$_1$-C$_{12}$-alkyl radicals which may be either unsubstituted or at least partly substituted by fluorine, chlorine, or unsubstituted or substituted aryl, or C$_1$-C$_6$-alkoxy. Alkyl more preferably represents branched, cyclic or acyclic C$_1$-C$_{12}$-alkyl radicals which are not further substituted.

Aryl represents, for example, carbocyclic aromatic radicals having from 6 to 18 skeleton carbon atoms or heteroaromatic radicals having from 5 to 18 skeleton carbon atoms, in which no, one, two or three skeleton carbon atoms per cycle, but at least one skeleton carbon atoms in the entire molecule, may be substituted by heteroatoms selected from the group of nitrogen, sulfur or oxygen. The carbocyclic aromatic radicals or heteroaromatic radicals may also be substituted by up to five identical or different substituents per cycle, selected from the group of free or protected hydroxyl, iodine, bromine, chlorine, fluorine, cyano, free or protected formyl, C$_1$-C$_{12}$-alkyl, for example methyl, ethyl, n-propyl, isopropyl, n-butyl, tert-butyl, cyclohexyl, n-hexyl, n-octyl or isooctyl, C$_6$-C$_{12}$-aryl, for example phenyl, C$_1$-C$_6$-alkoxy, tri(C$_1$-C$_6$-alkyl)siloxyl, for example trimethylsiloxyl, triethylsiloxyl and tri-n-butylsiloxyl.

Examples of carbocylic aromatic radicals having from 6 to 18 skeleton carbon atoms are, for example, phenyl, naphthyl, phenanthrenyl, anthracenyl or fluorenyl, heteroaromatic radicals having from 5 to 18 skeleton carbon atoms, in which no, one, two or three skeleton carbon atoms per cycle, but at least one skeleton carbon atom in the entire molecule, may be substituted by heteroatoms selected from the group of nitrogen, sulfur or oxygen, are, for example, pyridinyl, oxazolyl, thiophenyl, benzofuranyl, benzothiophenyl, dibenzofuranyl, dibenzothiophenyl, furanyl, indolyl, pyridazinyl, pyrazinyl, pyrimidinyl, thiazolyl, triazolyl or quinolinyl.

In the context of the invention, protected formyl is a formyl radical which has been protected by conversion to an aminal, acetal or a mixed aminal acetal, the aminals, acetals and mixed aminal acetals being acyclic or cyclic.

In the context of the invention, protected hydroxyl is a hydroxyl radical which has been protected by conversion to an acetal, carbonate, carbamate or carboxylate. Examples thereof are the conversion to a tetrahydropyranyl adduct, to a benzyloxycarbonyl derivative, allyloxycarbonyl derivative or a tert-butyloxycarbonyl derivative.

The areas of preference for compounds of the formula (I) are defined below.

$R^1$, $R^2$, $R^3$ and $R^4$ are preferably each independently hydrogen, methyl, ethyl, n-propyl, isopropyl, n-butyl and n-pentyl, more preferably hydrogen, methyl, ethyl, n-propyl and isopropyl, and most preferably each identically hydrogen.

R' and R" are preferably each independently, more preferably each identically, $C_3$-$C_8$-alkyl or $C_5$-$C_{10}$-aryl which is unsubstituted, monosubstituted or polysubstituted by radicals which are selected from the group of chlorine, fluorine, cyano, phenyl, $C_1$-$C_6$-alkoxy and $C_1$-$C_6$-alkyl, more preferably cyclopentyl, cyclohexyl, cycloheptenyl, phenyl, o-, m-, p-tolyl, 3,5-dimethylphenyl, 3,5-di-tert-butylphenyl, 3,5-dimethyl-4-methoxyphenyl, 3,5-di-tert-butyl-4-methylphenyl, 4-trifluoromethylphenyl, 4-fluorophenyl 2-, 3-furyl, 2-, 3-thiophenyl, 2-N-methylpyrrolyl, N-methyl-2-indolyl and 2-thiazolyl.

Particularly preferred compounds of the formula (I) include:

(R)- and (S)-[5,5'-dichloro-6,6'-(cis-1,4-but-2-enedioxy)biphenyl-2,2'-diyl]bis[(diphenyl)phosphine, (R)- and (S)-[5,5'-dichloro-6,6'-(cis-1,4-but-2-enedioxy)biphenyl-2,2'-diyl]bis[(dicyclohexyl)phosphine, (R)- and (S)-[5,5'-dichloro-6,6'-(cis-1,4-but-2-enedioxy)biphenyl-2,2'-diyl]bis[(di-3,5-di-tert-butyl-4-methoxyphenyl)phosphine, (R)- and (S)-[5,5'-dichloro-6,6'-(cis-1,4-but-2-enedioxy)biphenyl-2,2'-diyl]bis[(di-3,5-dimethylphenyl)phosphine, (R)- and (S)-[5,5'-dichloro-6,6'-(cis-1,4-but-2-enedioxy)biphenyl-2,2'-diyl]bis[(di-3,5-dimethyl-4-methoxyphenyl)phosphine, (R)- and (S)-[5,5'-dichloro-6,6'-(cis-1,4-but-2-enedioxy)biphenyl-2,2'-diyl]bis[(di-4-fluorophenyl)phosphine and also (R)- and (S)-[5,5'-dichloro-6,6'-(cis-1,4-but-2-enedioxy)biphenyl-2,2'-diyl]bis[(di-3,5-di-tert-butylphenyl)phosphine and also the corresponding trans compounds, preference being given to the cis compounds mentioned, and also (R)- and (S)-[5,5'-dichloro-6,6'-(1,3-propanedioxy)biphenyl-2,2'-diyl]bis[(diphenyl)-phosphine, (R)- and (S)-[5,5'-dichloro-6,6'-(1,3-propanedioxy)biphenyl-2,2'-diyl]bis[(dicyclohexyl)phosphine, (R)- and (S)-[5,5'-dichloro-6,6'-(1,3-propanedioxy)biphenyl-2,2'-diyl]bis[(di-3,5-di-tert-butyl-4-methoxyphenyl)-phosphine, (R)- and (S)-[5,5'-dichloro-6,6'-(1,3-propanedioxy)biphenyl-2,2'-diyl]bis[(di-3,5-dimethylphenyl)phosphine, (R)- and (S)-[5,5'-dichloro-6,6'-(1,3-propanedioxy)biphenyl-2,2'-diyl]bis[(di-3,5-dimethyl-4-methoxyphenyl)phosphine, (R)- and (S)-[5,5'-dichloro-6,6'-(1,3-propanedioxy)biphenyl-2,2'-diyl]bis[(di-4-fluorophenyl)phosphine and also (R)- and (S)-[5,5'-dichloro-6,6'-(1,3-propanedioxy)biphenyl-2,2'-diyl]bis[(di-3,5-di-tert-butylphenyl)phosphine, the stereoisomeric (R)- and (S)-[5,5'-dichloro-6,6'-(1,3-butanedioxy)biphenyl-2,2'-diyl]-bis(diphenylphosphines], the stereoisomeric (R) and (S)-[5,5'-dichloro-6,6'-(1,3-butanedioxy)biphenyl-2,2'-diyl]bis(diphenylphosphines) and also any mixtures of the enantiomers.

Inventive compounds of the formula (I) may be prepared, for example, in an analogous manner to processes known per se which have already been described for the synthesis of biphenylbisphosphines bridged in the 6,6'-position.

For example, the corresponding 6,6-dihydroxybisphosphines can be obtained, for example, from [5,5'-dichloro-6,6'-dimethoxybiphenyl-2,2'-diyl]bisphosphine or analogous compounds by ether cleavage and are subsequently converted by treatment with compounds of the formula (II)

$$X^1-B-X^2 \quad (II)$$

in which

B has the definition and areas of preference specified in the legend of formula (I) and in which $X^1$ and $X^2$ are each independently chlorine, bromine or iodine under conditions known per se (see, for example, J. Org. Chem. 2000, 65, 6224) to the inventive compounds of the formula (I).

To prepare compounds of the formula (I), the procedure is preferably that in a step a), compounds of the formula (V)

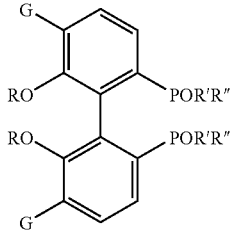

(V)

are converted by ether cleavage to compounds of the formula (III)

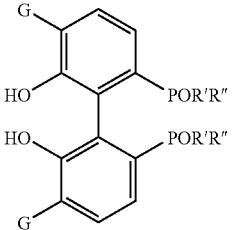

(III)

in a step b)

the compounds of the formula (III) are converted by reaction with compounds of the formula (II) in the presence of base to compounds of the formula (IV)

and in a step c)

the compounds of the formula (IV) are reduced to compounds of the formula (I)

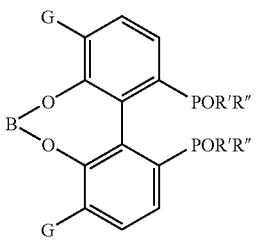
(IV)

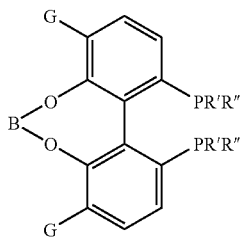
(I)

where B, G, R' and R" each have the same definitions and areas of preference as have already been defined under the formulae (I) and (II).

R in formula (V) is $C_1$-$C_6$-alkyl.

Unless enantiomerically enriched compounds of the formula (V) are used to prepare compounds of the formula (I), the compounds of the formula (IV) can preferably be separated into the stereoisomers in a manner known per se, for example by reacting with a chiral auxiliary reagent or by continuous or batchwise chromatography in the case of enantiomers on a chiral column material.

The ether cleavage in step a) may, for example, be effected in a manner known per se by reaction with $BBr_3$ and subsequent treatment with water.

The reaction of the compounds of the formula (III) with compounds of the formula (II) in step b) is preferably carried out in organic solvent in the presence of bases.

Suitable solvents are in particular alcohols, for example methanol, ethanol, propanol, ethylene glycol or ethylene glycol monomethyl ether, and amidic solvents, for example N,N-dimethylformamide, N,N-dimethyl acetamide or N-methylpyrrolidone or mixtures of the solvents mentioned.

The bases used may, for example, be alkali metal and alkaline earth metal compounds such as oxides, hydroxides, carbonates or alkoxides; examples include: calcium oxide, sodium hydroxide, potassium carbonate or sodium methoxide. It is also possible to use tertiary amines, for example triethylamine or tributylamine, as bases.

The molar ratio between compound of the formula (III) and compound of the formula (II) used is preferably between 1:1 and 1:4; in general, even a slight excess of compound of the formula (II) is sufficient for complete reaction. The base is preferably used in at least an equivalent amount to the compound of the formula (III). In the case of the use of bases insoluble in the solvent, for example of potassium carbonate in DMF, it is appropriate to use from four to ten times the molar amount and at the same time to ensure intensive mixing of the suspension.

The reaction in step b) may also be performed in a biphasic system, in which case the nonaqueous phase used comprises solvents in which the product of the formula (IV) formed is at least predominantly soluble; dichloromethane, for example, is suitable for this purpose. It is appropriate in this variant of the reaction to use phase transfer catalysts, for example quaternary ammonium or phosphine salts and tetrabutylammonium salts. Preference is given to tetrabutylammonium salts.

The reaction temperature in the reaction of compounds of the formula (III) to prepare the compounds of the formula (IV) may lie, for example, in the range from about 20° C. to 100° C., preferably in the range from 20° C. to 80° C.

The reduction of the compounds of the formula (IV) to the compounds of the formula (II) in step c) is carried out preferably by methods known per se. for example by reaction with trichlorosilane in inert solvents such as toluene or xylene and in the presence of tertiary amines such as tri-n-butylamine at reflux temperature (see, for example, EP-A 398 132, EP-A 749 973 and EP-A 926 152).

Moreover, the inventive compounds of the formula (IV) in which the substituent in the 6,6'-position is an alkenediyl radical may also be prepared by reacting the compounds of the formula (III) as defined above first with a compound of the formula (VIa) or (VIb) or successively with two different compounds of the formulae (VIa) and (VIb)

$X^3$—$(CHR^1)_n$—$(R^2C$=$CHR^5)$ (VIa)

$X^4$—$(CHR^4)_m$—$(R^3C$=$CHR^6)$ (VIb)

in which $X^3$ and $X^4$ are each chlorine, bromine, iodine or a sulfonate, preferably chlorine, bromine or iodine, and $R^1$, $R^2$, $R^3$ and $R^4$ are each as defined above including the areas of preference, and $R^5$ and $R^6$ are each independently hydrogen or $C_1$-$C_4$-alkyl to give compounds of the formula (VII)

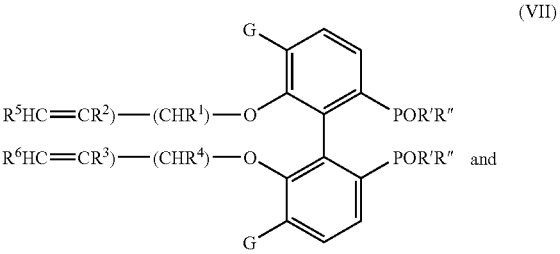
(VII)

and then converting the compounds of the formula (VII) in the presence of an olefin metathesis catalyst to compounds of the formula (IV).

The compounds of the formula (IV) may then be reduced in the above-described manner to the compounds of the formula (I).

For the reaction of the compounds of the formula (III) with compounds of the formula (VIa) and/or (VIb), the solvents, temperatures, molar ratios and other reaction parameters described for step b) of the former process apply in the same manner.

For the conversions of the compounds of the formula (VII) to compounds of the formula (IV), suitable olefin metathesis catalysts are in particular ruthenium-carbene complexes. Preferred ruthenium-carbene complexes are, for example, those of the formulae (Xa) and (Xb)

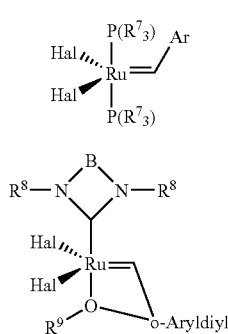

where, in formula (Xa),

Ar is aryl, Hal is chlorine, bromine or iodine, and $R^7$ is in each case independently $C_1$-$C_{12}$-alkyl, $C_5$-$C_{12}$-aryl or $C_6$-$C_{13}$-arylalkyl and where, in formula (Xb), o-aryldiyl is an ortho-divalent $C_5$-$C_{24}$-aryl radical which may also bear up to four radicals as have already been defined above for aryl, Hal is chlorine, bromine or iodine, B is an optionally mono- or di-$C_1$-$C_{12}$-alkyl-, —$C_5$-$C_{12}$-aryl- or —$C_6$-$C_{13}$-arylalkyl-substituted 1,2-ethanediyl or 1,2-ethenediyl, and $R^8$ is in each case independently $C_7$-$C_{12}$-alkyl, $C_5$-$C_{12}$-aryl or $C_6$-$C_{13}$-arylalkyl.

The latter process for preparing compounds of the formula (IV) is encompassed by the invention, as are the compounds of the formulae (IV) and (VII) required to prepare the compounds of the formula (I), both in the form of their pure stereoisomers and in any mixtures thereof, especially the racemic mixture.

The compounds of the formula (VII) include:

(R)- and (S)-[5,5'-dichloro-6,6'-(bisallyloxy)biphenyl-2,2'-diyl]bis[(di-cyclohexyl)-phosphine oxide, (R)- and (S)-[5,5'-dichloro-6,6'-(bisallyloxy)biphenyl-2,2'-diyl]bis[(di-3,5-di-tert-butyl-4-methoxyphenyl)phosphine oxide, (R)- and (S)-[5,5'-dichloro-6,6'-(bisallyloxy)biphenyl-2,2'-diyl]bis[(di-3,5-dimethylphenyl)phosphine oxide, (R)- and (S)-[5,5'-dichloro-6,6'-(bisallyloxy)biphenyl-2,2'-diyl]bis[(di-3,5-dimethyl-4-methoxyphenyl)phosphine oxide, (R)- and (S)-[5,5'-dichloro-6,6'-(bisallyloxy)biphenyl-2,2'-diyl]bis[(di-4-fluorophenyl)phosphine oxide and also (R)- and (S)-[5,5'-dichloro-6,6'-(bisallyloxy)biphenyl-2,2'-diyl]bis[(di-3,5-di-tert-butylphenyl)phosphine oxide.

Compounds of the formula (IV) include:

(R)- and (S)-[5,5'-dichloro-6,6'-(cis-1,4-but-2-enedioxy)biphenyl-2,2'-diyl]bis[(dicyclohexyl)phosphine oxide, (R)- and (S)-[5,5'-dichloro-6,6'-(cis-1,4-but-2-enedioxy)biphenyl-2,2'-diyl]bis[(di-3,5-di-tert-butyl-4-methoxyphenyl)phosphine oxide, (R)- and (S)-[5,5'-dichloro-6,6'-(cis-1,4-but-2-enedioxy)biphenyl-2,2'-diyl]bis[(di-3,5-dimethylphenyl)phosphine oxide, (R)- and (S)-[5,5'-dichloro-6,6'-(cis-1,4-but-2-enedioxy)biphenyl-2,2'-diyl]bis[(di-3,5-dimethyl-4-methoxyphenyl)]-phosphine oxide, (R)- and (S)-[5,5'-dichloro-6,6'-(cis-1,4-but-2-enedioxy)biphenyl-2,2'-diyl]bis[(di-4-fluorophenyl)phosphine oxide and also (R)- and (S)-[5,5'-dichloro-6,6'-(cis-1,4-but-2-enedioxy)biphenyl-2,2'-diyl]bis[(di-3,5-di-tert.-butylphenyl)phosphine oxide and also the corresponding trans compounds, preference being given to the cis compounds, and also (R)- and (S)-[5,5'-dichloro-6,6'-(1,3-propanedioxy)biphenyl-2,2'-diyl]bis[(di-cyclohexyl)phosphine oxide, (R)- and (S)-[5,5'-dichloro-6,6'-(1,3-propanedioxy)biphenyl-2,2'-diyl]bis[(di-3,5-di-tert-butyl-4-methoxyphenyl)phosphine oxide, (R)- and (S)-[5,5'-dichloro-6,6'-(1,3-propanedioxy)biphenyl-2,2'-diyl]bis[(di-3,5-dimethylphenyl)phosphine oxide, (R)- and (S)-[5,5'-dichloro-6,6'-(1,3-propanedioxy)biphenyl-2,2'-diyl]bis[(di-3,5-dimethyl-4-methoxyphenyl)phosphine oxide, (R)- and (S)-[5,5'-dichloro-6,6'-(1,3-propanedioxy)biphenyl-2,2'-diyl]bis[(di-4-fluorophenyl)phosphine oxide and also (R)- and (S)-[5,5'-dichloro-6,6'-(1,3-propanedioxy)biphenyl-2,2'-diyl]bis[(di-3,5-di-tert-butylphenyl)phosphine oxide, the stereoisomeric (R)-[5,5'-dichloro-6,6'-(1,3-butanedioxy)biphenyl-2,2'-diyl]bis(diphenylphosphine oxides), the stereoisomeric (S)-[5,5'-dichloro-6,6'-(1,3-butanedioxy)biphenyl-2,2'-diyl]bis(diphenylphosphine oxides) and also any mixtures of the enantiomers.

The compounds of the formula (I), preferably in stereoisomerically enriched form, are suitable in particular as ligands for the preparation of transition metal complexes which can be used as catalysts for processes for preparing enantiomerically enriched compounds.

The areas of preference for compounds of the formula (I) apply below in the same manner as described above.

The invention therefore encompasses both transition metal complexes comprising compounds of the formula (I) and catalysts which comprise the inventive transition metal complexes.

Preferred transition metal complexes are those which are obtainable by reaction of compounds of the formula (I) in the presence of transition metal compounds.

Preferred transition metal compounds are compounds of rhodium, iridium, ruthenium, palladium and nickel, greater preference being given to those of rhodium, iridium and ruthenium.

Preferred transition metal compounds are, for example, those of the formula (VIIIa)

$$M(Y^1)_3 \quad \text{(VIIIa)}$$

in which

M is ruthenium, rhodium, iridium and $Y^1$ is chloride, bromide, acetate, nitrate, methanesulfonate, trifluoromethanesulfonate or acetylacetonate and or transition metal compounds of the formula (VIIIb)

$$M(Y^2)_p B^1_2 \quad \text{(VIIIb)}$$

in which

M is ruthenium, rhodium, iridium and $Y^2$ is chloride, bromide, acetate, methanesulfonate, trifluoromethanesulfonate, tetrafluoroborate, hexafluorophosphate, perchlorate, hexafluoroantimonate, tetra(bis-3,5-trifluoromethylphenyl)borate or tetraphenylborate and P is 1 for rhodium and iridium and is 2 for ruthenium, $B^1$ in each case is a $C_2$-$C_{12}$-alkene, for example ethylene or cyclooctene, or a nitrile, for example acetonitrile, benzonitrile or benzyl nitrile, or $B^1_2$ together is a ($C_4$-$C_{12}$)-diene, for example norbornadiene or 1,5-cyclooctadiene or transition metal compounds of the formula (VIIIc)

$$[MB^2Y^1_2]_2 \quad \text{(VIIIc)}$$

in which

M is ruthenium and

B² represents aryl radicals, for example cymene, mesityl, phenyl or cyclooctadiene, norbornadiene or methylallyl or transition metal compounds of the formula (VIIId)

$$Me_3[M(Y^3)_4] \qquad (VIIId)$$

where

M is iridium or rhodium and

Y³ is chloride or bromide and

Me is lithium, sodium, potassium, ammonium or organic ammonium and or transition metal compounds of the formula (VIIIe)

$$[M(B^3)_2]An \qquad (VIIIe)$$

where

M is iridium or rhodium and

B³ is a (C₄-C₁₂)-diene, for example norbornadiene or 1,5-cyclooctadiene,

An is a noncoordinating or weakly coordinating anion, for example methanesulfonate, trifluoromethanesulfonate, tetrafluoroborate, hexafluorophosphate, perchlorate, hexafluoroantimonate, tetra(bis-3,5-trifluoromethylphenyl)borate or tetraphenylborate.

Further preferred transition metal compounds are cyclopentadienyl₂Ru, Rh(acac)(CO)₂, Ir(pyridine)₂(1,5-cyclooctadiene) or polynuclear bridged complexes, for example [Rh(1,5-cyclooctadiene)Cl]₂ and [Rh(1,5-cyclooctadiene)Br]₂, [Rh(ethene)₂Cl]₂, [Rh(cyclooctene)₂Cl]₂, [Ir(1,5-cyclooctadiene)Cl]₂ and [Ir(1,5-cyclooctadiene)Br]₂, [Ir(ethene)₂Cl]₂, and [Ir(cyclooctene)₂Cl]₂

The transition metal metal compounds used are most preferably:

[Rh(cod)Cl]₂, [Rh(cod)₂Br], [Rh(cod)₂]ClO₄, [Rh(cod)₂]BF₄, [Rh(cod)₂]PF₆, [Rh(cod)₂]OTf, [Rh(cod)₂]BAr₄ (Ar=3,5-bistrifluoromethylphenyl) [Rh(cod)₂]SbF₆ RuCl₂(cod), [(cymene)RuCl₂]₂, [(benzene)RuCl₂]₂, [(mesityl)RuCl₂]₂, [(cymene)RuBr₂]₂, [(cymene)RuI₂]₂, [(cymene)Ru(BF₄)₂]₂, [(cymene)Ru(PF₆)₂]₂, [(cymene)Ru(BAr₄)₂]₂, (Ar=3,5-bistrifluoromethylphenyl), [(cymene)Ru(SbF₆)₂]₂, [Ir(cod)₂Cl]₂, [Ir(cod)₂]PF₆, [Ir(cod)₂]ClO₄, [Ir(cod)₂]SbF₆ [Ir(cod)₂]BF₄, [Ir(cod)₂]OTf, [Ir(cod)₂]BAr₄ (Ar=3,5-bistrifluoromethylphenyl) RuCl₃, RhCl₃, [Rh(nbd)Cl]₂, [Rh(nbd)₂Br], [Rh(nbd)₂]ClO₄, [Rh(nbd)₂]BF₄, [Rh(nbd)₂]PF₆, [Rh(nbd)₂]OTf, [Rh(nbd)₂]BAr₄ (Ar=3,5-bistrifluoromethylphenyl) [Rh(nbd)₂]SbF₆ RuCl₂(nbd), [Ir(nbd)₂]PF₆, [Ir(nbd)₂]ClO₄, [Ir(nbd)₂]SbF₆ [Ir(nbd)₂]BF₄, [Ir(nbd)₂]OTf, [Ir(nbd)₂]BAr₄ (Ar=3,5-bistrifluoromethylphenyl), Ir(pyridine)₂(nbd), RuCl₃, [Ru(DMSO)₄Cl₂], [Ru(CH₃CN)₄Cl₂], [Ru(PhCN)₄Cl₂], [Ru(cod)Cl₂]ₙ, [Ru(cod)(methallyl)₂] and [Ru(acetylacetonate)₃].

Particularly preferred transition metal complexes are those of the formulae (VIIIa, b, c)

$$[M(I)Hal]_2 \qquad (VIIa)$$

$$[M(cod)(I)]An \qquad (VIIIb)$$

$$[M(nbd)(I)]An \qquad (VIIIc)$$

in which

M is rhodium or iridium and

Hal is chloride, bromide or iodide and (I) is a compound of the formula (I) and

An is a noncoordinating or weakly coordinating anion, for example methanesulfonate, trifluoromethanesulfonate, tetrafluoroborate, hexafluoro-phosphate, perchlorate, hexafluoroantimonate, tetra(bis-3,5-trifluoromethyl-phenyl)borate or tetraphenylborate and compounds of the formulae (IXa, b, c, d, e, f)

$$[Ru(AcO)_2(I)] \qquad (IXa)$$

$$[Ru_2Cl_4(I)_2NEt_3] \qquad (IXb)$$

$$[RuHal(I)(AR)]_2 \qquad (IXc)$$

$$[Ru(I)](An)_2 \qquad (IXd)$$

$$[\{RuHal(I)\}_2(\mu\text{-}Hal)_3]^-[(R''')_2NH_2]^+ \qquad (IXe)$$

$$[RuHal_2(I)(diamine)] \qquad (IXf)$$

in which

Hal is chloride, bromide or iodide and (I) is a compound of the formula (I) and

An is a noncoordinating or weakly coordinating anion, for example methanesulfonate, trifluoromethanesulfonate, tetrafluoroborate, hexafluorophosphate, perchlorate, hexafluoroantimonate, tetra(bis-3,5-trifluoromethylphenyl)borate or tetraphenylborate and R''' is in each case independently C₁-C₆-alkyl and diamine represents chiral 1,2-diamines which are preferably selected from the group of (S,S)- and (R,R)-1,2-diphenylethylenediamine and (R)- or (S)-1,1-bis(4-methoxyphenyl)-3-methyl-1,2-butanediamine and AR is an arene ligand which is preferably selected from the group of benzene, p-cymene and mesitylene.

The preparation of such complex types is known in principle and is possible, for example, analogously to Chemistry Letters, 1851, 1989; J. Organomet. Chem., 1992, 428, 213 (VIIIa,b,c); J. Chem. Soc., Chem. Commun., 922, 1985 (IXa, b,c,d), EP-A 945 457 (IXe) and Pure Appl. Chem., Vol. 71,8, 1493-1501, 1999 (IXf).

The inventive transition metal complexes and catalysts are suitable in particular for use in a process for the transition metal-catalyzed preparation of enantiomerically enriched compounds and for C═C double bond isomerizations, which is likewise encompassed by the invention.

It is possible to use either isolated transition metal complexes, for example those of the formulae (VIIIa-c) and (IXa-e) or transition metal complexes prepared in situ, preference being given to the latter.

Preference is given to using the transition metal complexes and catalysts for asymmetric hydrogenations. Preferred asymmetric hydrogenations are, for example, hydrogenations of prochiral C═C bonds, for example prochiral enamines, olefins, enol ethers, C═O bonds, for example prochiral ketones, and C═N bonds, for example prochiral imines. Particularly preferred asymmetric hydrogenations are hydrogenations of prochiral ketones, especially alpha- and beta-keto esters, for example methyl or ethyl chloroacetate and also methyl or ethyl acetoacetate.

The amount of the transition metal compound used or of the transition metal complex used may, for example, be from 0.001 to 5 mol % based on the substrate used, preferably from 0.01 to 2 mol %.

The enantiomerically enriched compounds preparable in accordance with the invention are suitable in particular for preparing agrochemicals, pharmaceuticals or intermediates thereof.

The advantage of the present invention is that, with the aid of the inventive catalysts, enantioselectivities and activities are achieved which have to date not been achievable with similar catalysts.

EXAMPLES

Example 1

Preparation of (S)-[5,5'-dichloro-6,6'-dihydroxybiphenyl-2,2'-diyl]bis(diphenyl-phosphine oxide)

3.4 ml of $BBr_3$ (=8.77 g) were added dropwise with stirring to a solution of 8 g of (S)-[5,5'-dichloro-6,6'-dimethoxybiphenyl-2,2'-diyl]bis(diphenylphosphine oxide) in 160 ml of methylene chloride dried over $CaH_2$, which had been cooled to −78° C. in a stirred vessel with exclusion of moisture, and the reaction mixture was kept at this temperature for 1 hour. The temperature was then allowed to rise to room temperature within 2 hours and the mixture was stirred at this temperature for a further 24 hours. Under ice cooling, a total of 50 ml of water were subsequently added dropwise with good mixing within 1 hour, then the methylene chloride was distilled off and, after addition of a further 110 ml of water, the mixture was kept at 80° C. with stirring for 6 hours. After cooling to RT, the resulting precipitate was filtered off with suction through a glass filter frit, and washed with 100 ml of water and then with 200 ml of methylene chloride with intensive mixing. After the drying of the remaining product, 6.3 g (=82% of theory) of pure (S)-[5,5'-dichloro-6,6'-dihydroxybiphenyl-2,2'-diyl]bis(diphenylphosphine oxide) were obtained, m.p. 236-237° C.

Obtained in addition to 38 mg of the intermediate used were 123 mg of (S)-cis compound of the above-specified formula m.p. 126° C.-128° C., $[a]_D$=+57.6° (c=1.0, $CHCl_3$) and 118 mg of the (S)-trans compound of the above-specified formula m.p. 141° C.-142° C., $[a]_D$=−48.4° (c=1.4, $CHCl_3$).

Example 2

Preparation of cis- and trans-(S)-[5,5'-dichloro-6,6'-(1,4-but-2-enedioxy)biphenyl-2,2'-diyl]bis(diphenylphosphine oxide)

A mixture of 0.50 g (0.76 mmol) of (S)-[5,5'-dichloro-6,6'-dihydroxybiphenyl-2,2'-diyl]bis(diphenylphosphine oxide) and of 0.42 g (3.04 mmol) of potassium carbonate in 10 ml of DMF is stirred intensively at room temperature for 30 minutes. With further intensive stirring, 0.223 g (3.04 mmol) of allyl chloride is added and this mixture is kept at 40° C. for 26 hours. Subsequently, the reaction mixture is worked up analogously to the procedure described in Example 1. In addition to 0.136 g of the dichlorodihydroxybiphenylphosphine oxide and 58 mg of a mixed fraction of monoallyloxy- and bisallyloxydichlorobisphenylbisphosphine oxide, 0.395 g of pure (S)-[6,6'-bisallyloxy-5,5'-dichlorobiphenyl-2,2'-diyl]bis(diphenylphosphine oxide) is obtained.

m.p. 214° C.-215° C. (decomposes), $[a]_D$=−56.8° (c=1.0, $CHCl_3$).

295 mg of the above-described intermediate dissolved in 40 ml of $CH_2Cl_2$ are added dropwise at room temperature and under an argon atmosphere over one hour to a solution of 18 mg of 1st generation Grubbs catalyst in 40 ml of dry $CH_2Cl_2$. Afterward, the mixture is kept under reflux at 40° C. for 5 hours and at room temperature over 24 hours. Subsequently, the catalyst is destroyed by stirring under air (1 hour) and the resulting product mixture is filtered through silica gel, and the crude product is separated chromatographically analogously to the procedure in Example 1.

Example 3

Preparation of (R)-(1,4-but-2-enedioxy)biphenyl-2,2'-diyl]bis(diphenylphosphine oxide)

A mixture of 4.1 g (6.99 mmol) of (R)-(6,6'-dihydroxybiphenyl-2,2'-diyl)bis(diphenylphosphine oxide) and 3.85 g (27.96 mmol) of potassium carbonate in 50 ml of dimethylformamide is stirred at room temperature intensively for 1 hour. Afterward, 0.96 g (7.69 mmol) of cis-1,1-dichlorobut-2-ene dissolved in 5.0 ml of DMF is added dropwise to the still intensively stirred mixture, and the mixture is stirred at RT for a further 12 hours and at 80° C. for 8 hours. After cooling, the reaction mixture is filtered.

After acidification with 2N hydrochloric acid, 0.71 g of the dihydroxybisphenyl-bisphosphine oxide is recovered unchanged in pure form from the precipitate which has been filtered off.

The filtrate is carefully brought to dryness with heating to 60° C. at 0.5 mbar and subsequently dissolved in 60 ml of dry dichloromethane. After 12 hours, this solution is filtered with addition of silica gel as a filtration aid. A further 0.13 g of the bisphosphine oxide used is recovered from the solid product which has been filtered off.

The filtrate is concentrated by evaporation to afford 3.41 g of a crude product which is separated by chromatography (Merck 9385 silica gel, eluent: ethyl acetate/methanol/water, 500:50:5). 2.76 g of pure product of the above-specified formula are obtained.

m.p. 116° C.-118° C., $[a]_D$=−161.1° (c=1.0, $CHCl_3$).

Example 4

Analogously to Example 3, (S)-cis-[6,6'-(1,6-hex-3-enedioxy)biphenyl-2,2'-diyl']bis(diphenylphosphine oxide) is m.p. 234° C.-235° C., $[a]_D$=−99° (c=0.5, EtOH).

Example 5

Analogously to Example 3, (R)-trans-[6,6'-(1,4-but-2-enedioxy)biphenyl-2,2'-diyl']bis(diphenylphosphine oxide) is m.p. 192° C.-194° C. (decomposes), $[a]_D$=+86.8° (c=0.5, $CHCl_3$).

Example 6

Preparation of (R)-cis-[6,6'-(1,4-but-2-enedioxy)biphenyl-2,2'-diyl]bis(diphenyl)-phosphine The phosphine oxide from Example 3 (0.686 g, 1 mmol) was initially charged with xylene (18 ml) under argon, and the resulting mixture was first admixed with tri(n-butyl)amine (3.5 ml, 15 mmol) and trichlorosilane (1.5 ml, 15 mmol) and then heated under reflux for 2 hours. The mixture was allowed to cool and stirred briefly with degassed NaOH solution (30%, 15 ml), 25 ml of degassed water were added and the phases were separated. The aqueous phase was extracted 3 times with methyl tert-butyl ether (10 ml) and the combined organic phases were first washed with sat. sodium chloride solution and then dried over MgSO$_4$. The organic solvent was removed under reduced pressure and the product was obtained as a colorless powder.

Yield: 95% of theory.

Example 7

Preparation of (S)-cis-[6,6'-(1,4-hex-3-enedioxy) biphenyl-2,2'-diyl]bis(diphenyl)-phosphine The phosphine oxide from Example 4 was reduced entirely analogously to Example 6 and obtained in a yield of 91%.

Example 8

Preparation of (S)-cis-[5,5'-dichloro-6,6'-(1,4-but-2-enedioxy)biphenyl-2,2'-diyl]bis(diphenyl)phosphine The phosphine oxide from Example 2 was reduced entirely analogously to Example 6 and obtained in a yield of 94%.

Enantioselective Hydrogenation of Methyl Acetoacetate (S1)

Example 9

(S)-cis-[6,6'-(1,4-Hex-3-enedioxy)biphenyl-2,2'-diyl]bis (diphenyl)phosphine (4.4 mg, 2 mol %), RuCl$_3$ (1.4 mg, 1 mol %) and 75 mg of S1 were initially charged in methanol (1.3 ml) and the mixture was heated to 50° C. under a hydrogen pressure of 10 bar for 23 h. After this time, an enantiomeric purity of the product of 97.3% ee was determined.

Example 10

(R)-cis-[6,6'-(1,4-But-3-enedioxy)biphenyl-2,2'-diyl]bis (diphenyl)phosphine (4.4 mg, 2 mol %), RuCl$_3$ (1.4 mg, 1 mol %) and 75 mg of S1 were initially charged in methanol (1.3 ml) and the mixture was heated to 50° C. under a hydrogen pressure of 10 bar for 23 h. After this time, an enantiomeric purity of the product of 98.6% ee was determined.

Example 11

(S)-cis-[5,5'-(1,4-Dichloro-6,6'-(1,4-but-3-enedioxy)biphenyl-2,2'-diyl]bis(diphenyl)-phosphine (4.4 mg, 2 mol %), RuCl$_3$ (1.4 mg, 1 mol %) and 75 mg of S1 were initially charged in methanol (1.3 ml) and the mixture was heated to 50° C. under a hydrogen pressure of 10 bar for 5 h. After this time, an enantiomeric purity of the product of 98.3% ee was determined.

Example 12 (for Comparison)

(S)-[5,5'-Dichloro-6,6'-dimethoxybiphenyl-2,2'-diyl]bis (diphenyl)phosphine (4.4 mg 2 mol %), RuCl$_3$ (1.4 mg, 1 mol %) and 75 mg of S1 were initially charged in methanol (1.3 ml) and the mixture was heated to 50° C. under a hydrogen pressure of 10 bar for 23 h. After this time, an enantiomeric purity of the product of 96.4% ee was determined.

Example 13

Preparation of (S)-[5,5'-dichloro-6,6'-(1,3-propanedioxy)biphenyl-2,2'-diyl]bis(diphenylphosphine oxide)

1.69 g of 1,3-dibromopropane were added at 22° C. to a solution or suspension, mixed effectively using an intensive stirrer, of 5.0 g of (S)-[5,5'-dichloro-6,6'-dihydroxybiphenyl-2,2'-diyl]bis(diphenylphosphine oxide) and of 4.2 g of potassium carbonate in 75 ml of DMF. Afterward, the reaction mixture was stirred at room temperature for a further 72 hours and then filtered. The solvent was removed from the filtrate by vacuum distillation. The (S)-[5,5'-dichloro-6,6'-bis(3-bromopropoxy)biphenyl-2,2'-diyl]bis(diphenylphosphine oxide) (0.34 g) formed as a by-product was removed chromatographically (Merck 9385 silica gel, eluent: ethyl acetate/hexane/methanol, 10:1:1). After this chromatography, the main product still received a small amount of the substrate used as an impurity. To remove these impurities, this product was dissolved in 40 ml of DMF, 160 mg of potassium carbonate and 0.15 ml of methyl bromoacetate were added, and the mixture was stirred at room temperature overnight. After filtration and removal of the solvent by evaporating it off under reduced pressure, the resulting product was separated chromatographically under the same conditions as specified above. 4.0 g of pure product of the above-specified formula were obtained.

m.p. 135°-137° C. [a]$_D$=+151.3° (c=1.0, CHCl$_3$).

Example 14

Preparation of (S)-[5,5'-dichloro-6,6'-(1,4-butanedioxy)biphenyl-2,2'-diyl]bis(diphenylphosphine oxide)

0.329 g of 1,4-dibromobutane was added at 22° C. to a solution or suspension, mixed efficiently using an intensive stirrer, of 1.0 g of (S)-[5,5'-dichloro-6,6'-dihydroxybiphenyl-2,2'-diyl]bis(diphenylphosphine oxide) and of 0.84 g of potassium carbonate in 25 ml of DMF. Afterward, the reaction mixture was stirred first at room temperature for 12 hours and then at 80° C. for a further 36 hours. Subsequently, the resulting product mixture was filtered and the solvent was removed from the filtrate by vacuum distillation.

The thus obtained product was separated chromatographically (Merck 9385 silica gel, eluent: ethyl acetate/hexane/methanol, 75:1.5:1.0). 0.67 g of pure product of the above of the above-specified formula was obtained.

m.p. 138°-140° C., [a]$_D$=+15.2° (c=1.0, CHCl$_3$)

Example 15

Preparation of the stereoisomers of (S)-[5,5'-dichloro-6,6'-(1,3-butanedioxy)biphenyl-2,2'-diyl]bis (diphenylphosphine oxide)

A solution or suspension of 250 mg of (S)-[5,5'-dichloro-6,6'-dihydroxybiphenyl-2,2'-diyl]bis(diphenylphosphine oxide) and of 210 mg of potassium carbonate and also of 90 mg of racemic 1,3-dibromobutane in 5.0 ml of DMF was stirred intensively at room temperature for 12 hours and then at 80° C. for 10 hours. Afterward, the reaction mixture was filtered and the resulting filtrate was concentrated to dryness under reduced pressure. Two pure diastereomers, each of which corresponds to the above-specified formula, were isolated in pure form from the resulting crude product by chromatography (Merck 9385 silica gel, eluent: ethyl acetate/hexane/methanol, 75.0:1.5:1.0).

Diastereomer 4A (64 mg):
    m.p. 132°-135° C. $[a]_D$=+62.4° (c=1.0, $CHCl_3$).

Diastereomer 4B (42 mg):
    m.p. 118°-119° C. $[a]_D$=+137.7° (c=1.0, $CHCl_3$).

Example 16

Preparation of (S)-[5,5'-dichloro-6,6'-(1,4-butanedioxy)biphenyl-2,2'-diyl]-bis(diphenyl)phosphine The phosphine oxide from Example 14 (0.687 g, 1 mmol) was initially charged with xylene (18 ml) under argon, and the resulting mixture was first admixed with tri(n-butyl)amine (3.5 ml, 15 mmol) and trichlorosilane (1.5 ml, 15 mmol) and then heated under reflux for 2 hours. The mixture was allowed to cool and stirred briefly with degassed NaOH solution (30%, 14 ml), 20 ml of degassed water were added and the phases were separated. The aqueous phase was extracted 4 times with methyl tert-butyl ether (MTBE) and the combined organic phases were first washed with sat. sodium chloride solution and then dried over $MgSO_4$. The organic solvent was removed under reduced pressure and the product was obtained as a colorless powder.
    Yield: 97% of theory
    $^{31}$P-NMR (161.9 MHz, $CDCl_3$): −13.61 ppm.

Example 17

Preparation of (S)-[5,5'-dichloro-6,6'-(1,3-propanedioxy)biphenyl-2,2'-diyl]-bis(diphenyl)phosphine Exactly analogously to Example 16, the product was obtained in 98% yield.
    $^{31}$P-NMR (161.9 MHz, $CDCl_3$): −10.91 ppm.

Enantioselective Hydrogenations of Ethyl Chloroacetoacetate (S2) and Methyl Acetoacetate (S3)

Example 18

(S)-[5,5'-Dichloro-6,6'-(1,3-propanedioxy)biphenyl-2,2'-diyl]bis(diphenyl)phosphine (3.2. mg, 0.02 mol %), [(p-cumene)$RuCl]_2$ (1.5 mg, 0.01 mol %) and 4 g of S2 were initially charged in ethanol (10 ml) and the mixture was heated under a hydrogen pressure of 90 bar to 80° C. for 1 h. After this time, an enantiomeric purity of the product of 96.5% ee was determined.

Example 19 (for Comparison)

(S)-[5,5'-Dichloro-6,6'-dimethoxybiphenyl-2,2'-diyl]bis(diphenyl)phosphine (3.2 mg, 0.02 mol %), [(p-cumene)$RuCl]_2$ (1.5 mg, 0.01 mol %) and 4 g of S2 were initially charged in ethanol (10 ml) and the mixture was heated under a hydrogen pressure of 90 bar to 80° C. for 1 h. After this time, an enantiomeric purity of the product of 95.1% ee was determined.

Example 20

(S)-[5,5'-Dichloro-6,6'-(1,4-butanedioxy)biphenyl-2,2'-diyl]bis(diphenyl)phosphine (4.4 mg, 2 mol %), $RuCl_3$ (1.4 mg, 1 mol %) and 75 mg of S3 were initially charged in methanol (1.3 ml) and the mixture was heated under a hydrogen pressure of 10 bar to 50° C. for 5 h. After this time, an enantiomeric purity of the product of 97.1% ee was determined.

Example 21 (for Comparison)

(S)-[5,5'-dichloro-6,6'-dimethoxybiphenyl-2,2'-diyl]bis(diphenyl)phosphine (4.4 mg, 2 mol %), $RuCl_3$ (1.4 mg, 1 mol %) and 75 mg of S3 were initially charged in methanol (1.3 ml) and the mixture was heated under a hydrogen pressure of 10 bar to 50° C. for 5 h. After this time, an enantiomeric purity of the product of 96.4% ee was determined.

What is claimed is:
1. A compound of the formula (I)

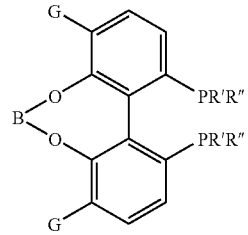

in which B is a bivalent moiety of the formula —$(CHR^1)_n$—$(R^2C$=$CR^3)$—$(CHR^4)_m$ where $R^1$, $R^2$, $R^3$ and $R^4$ are each independently hydrogen or alkyl, and n and m are each independently zero or an integer from 1 to 8, where, however, the sum of n and m is from 1 to 8, and in which, moreover, G is chlorine or hydrogen and R' and R" are each independently aryl or alkyl or in which B is a bivalent moiety of the formula —$(CHR^1)_n$—$(CR^2R^3)_m$—$(CHR^4)_o$ where $R^1$, $R^2$, $R^3$ and $R^4$ are each independently hydrogen or alkyl, and n, m and o are each independently zero or an integer from 1 to 8, where the sum of n, m and o is from 1 to 8, G is chlorine and R' and R" are each independently aryl or alkyl.

2. The compound as claimed in claim 1, characterized in that $R^1$, $R^2$, $R^3$ and $R^4$ are each independently hydrogen, methyl, ethyl, n-propyl, isopropyl, n-butyl and n-pentyl.

3. The compound as claimed in claim 1, characterized in that R' and R" are each independently $C_3$-$C_8$-alkyl or $C_5$-$C_{10}$-aryl which may be unsubstituted, monosubstituted or polysubstituted by radicals which are selected from the group of chlorine, fluorine, cyano, phenyl, $C_1$-$C_6$-alkoxy and $C_1$-$C_6$-alkyl.

4. The compound as claimed in claim 1, characterized in that they are the following:
    (R)- and (S)-[5,5'-dichloro-6,6'-(cis-1,4-but-2-enedioxy)biphenyl-2,2'-diyl]bis[(diphenyl)phosphine, (R)- and (S)-[5,5'-dichloro-6,6'-(cis-1,4-but-2-enedioxy)biphenyl-2,2'-diyl]bis[(dicyclohexyl)phosphine, (R)- and (S)-[5,5'-dichloro-6,6'-(cis-1,4-but-2-enedioxy)biphenyl-2,2'-diyl]bis[(di-3,5-di-tert-butyl-4-methoxyphenyl)phosphine, (R)- and (S)-[5,5'-dichloro-6,6'-(cis-1,4-but-2-enedioxy)biphenyl-2,2'-diyl]bis[(di-3,5-dimethylphenyl)phosphine, (R)- and (S)-[5,5'-dichloro- 6,6'-(cis-1,4-but-2-enedioxy)biphenyl-2,2'-diyl]bis[(di-3,5-dimethyl-4-methoxyphenyl)phosphine, (R)- and (S)-[5,5'-dichloro-6,6'-(cis-1,4-but-2-enedioxy)biphenyl-2,2'-diyl]bis[(di-4-fluorophenyl)phosphine and also (R)- and (S)-[5,5'-dichloro-6,6'-(cis-1,4-but-2-enedioxy)biphenyl-2,2'-diyl]bis[(di-3,5-di-tert-butylphenyl)phosphine and also the corresponding trans compounds, (R)- and (S)-[5,5'-dichloro-6,6'-(1,3-propanedioxy)biphenyl-2,2'-diyl]bis[(diphenyl)phosphine, (R)- and (S)-[5,5'-dichloro-6,6'-(1,3-propanedioxy)biphenyl-2,2'-diyl]bis[(dicyclohexyl)phosphine, (R)- and (S)-[5,5'-dichloro-6,6'-(1,3-propanedioxy)biphenyl-2,2'-diyl]bis[(di-3,5-di-tert-butyl-4-methoxyphenyl)-phosphine, (R)- and (S)-[5,5'-dichloro-6,6'-(1,3-propanedioxy)biphenyl-2,2'-diyl]bis[(di-3,5-dimethylphenyl)phosphine, (R)- and (S)-[5,5'-dichloro-6,6'-(1,3-propanedioxy)biphenyl-2,2'-diyl]bis[(di-3,5-dimethyl-4-methoxyphenyl)phosphine, (R)- and (S)-[5,5'-dichloro-6,6'-(1,3-propanedioxy)biphenyl-2,2'-diyl]bis[(di-4-fluorophenyl)phosphine and also (R)- and (S)-[5,5'-dichloro-6,6'-(1,3-propanedioxy)biphenyl-2,2'-diyl]bis[(di-3,5-di-tert-butylphenyl)phosphine, the stereoisomeric (R)- and (S)-[5,5'-dichloro-6,6'-(1,3-butanedioxy)biphenyl-2,2'-diyl]-bis(diphenylphosphines], the stereoisomeric (R) and (S)-[5,5'-dichloro-6,6'-(1,3-butanedioxy)biphenyl-2,2'-diyl]bis(diphenylphosphines) and also any mixtures of the enantiomers.

5. A process for preparing compounds of the formula (IV)

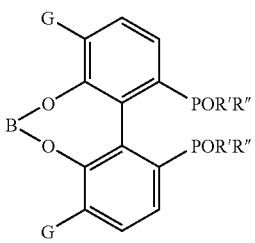

(IV)

in which B, G, R' and R" are each as defined in claim 1, characterized in that compounds of the formula (III)

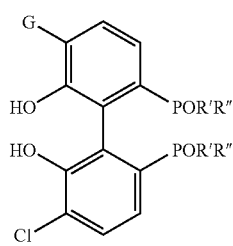

(III)

are reacted with a compound of the formula (VIa) or (VIb) or successively with two different compounds of the formulae (VIa) and (VIb)

$$X^3-(CHR^1)_n-R^2C=CHR^5 \quad (VIa)$$

$$X^4-(CHR^4)_m-R^3C=CHR^6 \quad (VIb)$$

in which $X^3$ and $X^4$ are each chlorine, bromine, iodine or a sulfonate and $R^1$, $R^2$, $R^3$, $R^4$, m, and n, are each as defined in claim 1, and $R^5$ and $R^6$ are each independently hydrogen or $C_1$-$C_4$-alkyl to give compounds of the formula (VII)

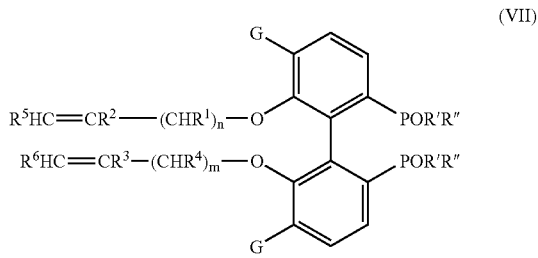

(VII)

and the compounds of the formula (VII) are then converted in the presence of an olefin metathesis catalyst to compounds of the formula (IV).

6. The process as claimed in claim 5, characterized in that the compounds of the formula (VII) are subsequently reduced to compounds of the formula (I) as claimed in claim 1.

7. The compound of the formula (VII)

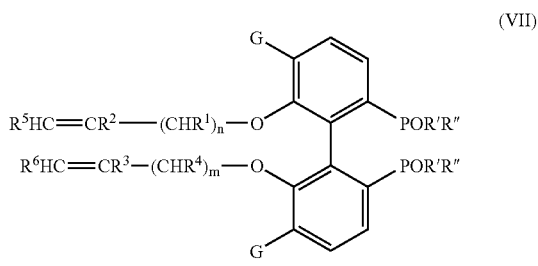

(VII)

in which G, $R^1$, $R^2$, $R^3$, $R^4$, R', R", n, and m are each as defined in claim 1 and $R^5$ and $R^6$ are each independently hydrogen or $C_1$-$C_4$-alkyl.

8. The compound as claimed in claim 7, characterized in that they are the following:

(R)- and (S)-[5,5'-dichloro-6,6'-(bisallyloxy)biphenyl-2,2'-diyl]bis[(di-cyclohexyl)phosphine oxide, (R)- and (S)-[5,5'-dichloro-6,6'-(bisallyloxy)-biphenyl-2,2'-diyl]bis[(di-3,5-di-tert-butyl-4-methoxyphenyl)phosphine oxide, (R)- and (S)-[5,5'-dichloro-6,6'-(bisallyloxy)biphenyl-2,2'-diyl]bis[(di-3,5-dimethylphenyl)phosphine oxide, (R)- and (S)-[5,5'-dichloro-6,6'-(bisallyloxy)biphenyl-2,2'-diyl]bis[(di-3,5-dimethyl-4-methoxyphenyl)-phosphine oxide, (R)- and (S)-[5,5'-dichloro-6,6'-(bisallyloxy)biphenyl-2,2'-diyl]bis[(di-4-fluorophenyl)phosphine oxide and also (R)- and (S)-[5,5'-dichloro-6,6'-(bisallyloxy)biphenyl-2,2'-diyl]bis[(di-3,5-di-tert-butylphenyl)phosphine oxide.

9. A compound of the formula (IV)

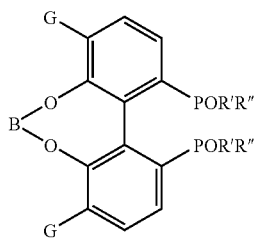

(IV)

in which B, R' and R" are each as defined in claim 1.

10. The compound as claimed in claim 9, characterized in that they are the following:

(R)- and (S)-[5,5'-dichloro-6,6'-(cis-1,4-but-2-enedioxy) biphenyl-2,2'-diyl]bis[(dicyclohexyl)phosphine oxide, (R)- and (S)-[5,5'-dichloro-6,6'-(cis-1,4-but-2-enedioxy)biphenyl-2,2'-diyl]bis[(di-3,5-di-tert-butyl-4-methoxy-phenyl)phosphine oxide, (R)- and (S)-[5,5'-dichloro-6,6'-(cis-1,4-but-2-enedioxy)biphenyl-2,2'-diyl]bis[(di-3,5-dimethylphenyl)phosphine oxide, (R)- and (S)-[5,5'-dichloro-6,6'-(cis-1,4-but-2-enedioxy)biphenyl-2,2'-diyl]bis[(di-3,5-dimethyl-4-methoxyphenyl)phosphine oxide, (R)- and (S)-[5,5'-dichloro-6,6'-(cis-1,4-but-2-enedioxy)biphenyl-2,2'-diyl]bis[(di-4-fluorophenyl)phosphine oxide and also (R)- and (S)-[5,5'-dichloro-6,6'-(cis-1,4-but-2-enedioxy)biphenyl-2,2'-diyl]bis[(di-3,5-di-tert.-butylphenyl)phosphine oxide and also the corresponding trans compounds and also (R)- and (S)-[5,5'-dichloro-6,6'-(1,3-propanedioxy)biphenyl-2,2'-diyl]bis[(di-cyclohexyl)phosphine oxide, (R)- and (S)-[5,5'-dichloro-6,6'-(1,3-propanedioxy)biphenyl-2,2'-diyl]bis[(di-3,5-di-tert-butyl-4-methoxyphenyl)phosphine oxide, (R)- and (S)-[5,5'-dichloro-6,6'-(1,3-propanedioxy)biphenyl-2,2'-diyl]bis[(di-3,5-dimethylphenyl)phosphine oxide, (R)- and (S)-[5,5'-dichloro-6,6'-(1,3-propanedioxy)biphenyl-2,2'-diyl]bis[(di-3,5-dimethyl-4-methoxyphenyl)phosphine oxide, (R)- and (S)-[5,5'-dichloro-6,6'-(1,3-propanedioxy)biphenyl-2,2'-diyl]bis[(di-4-fluorophenyl)phosphine oxide and also (R)- and (S)-[5,5'-dichloro-6,6'-(1,3-propanedioxy)biphenyl-2,2'-diyl]bis[(di-3,5-di-tert-butylphenyl)phosphine oxide, the stereoisomeric (R)-[5,5'-dichloro-6,6'-(1,3-butanedioxy)biphenyl-2,2'-diyl]-bis(diphenylphosphine oxides), the stereoisomeric (S)-[5,5'-dichloro-6,6'-(1,3-butanedioxy)biphenyl-2,2'-diyl]bis(diphenylphosphine oxides) and also any mixtures of the enantiomers.

11. A transition metal complex comprising compounds according to claim 1.

12. A catalyst comprising transition metal complex as claimed in claim 11.

13. A process for the asymmetrical hydrogenation of prochiral C═C bonds, C═O bonds, or C═N bonds comprising hydrogenating the prochiral C═C bonds, C═O bonds, or C═N bonds in the presence of a catalyst according to claim 12.

* * * * *